(12) United States Patent
Gammons

(10) Patent No.: US 8,245,487 B2
(45) Date of Patent: Aug. 21, 2012

(54) PACKAGING SYSTEM FOR A STERILIZABLE ITEM

(75) Inventor: Clifford E. Gammons, Loudon, TN (US)

(73) Assignee: Adroit Development, Inc., Loudon, TN (US)

( * ) Notice: Subject to any disclaimer, the term of this patent is extended or adjusted under 35 U.S.C. 154(b) by 0 days.

(21) Appl. No.: 13/025,146

(22) Filed: Feb. 10, 2011

(65) Prior Publication Data

US 2011/0192115 A1 Aug. 11, 2011

Related U.S. Application Data

(60) Provisional application No. 61/303,435, filed on Feb. 11, 2010.

(51) Int. Cl.
*B65B 55/02* (2006.01)

(52) U.S. Cl. .................. 53/425; 53/460; 53/570; 422/1

(58) Field of Classification Search ............ 53/425, 53/460, 464, 469, 491, 570; 422/1, 28, 460
See application file for complete search history.

(56) References Cited

U.S. PATENT DOCUMENTS

| 3,107,786 | A | * | 10/1963 | Adelman | 206/278 |
| 3,224,640 | A | * | 12/1965 | Schneider et al. | 222/107 |
| 3,494,726 | A | * | 2/1970 | Barasch | 422/29 |
| 4,358,015 | A | | 11/1982 | Hirsch | |
| 4,705,171 | A | * | 11/1987 | Eldridge | 206/438 |
| 5,638,661 | A | | 6/1997 | Banks | |
| 6,436,341 | B1 | | 8/2002 | Gammons et al. | |
| 6,672,036 | B2 | * | 1/2004 | Banks | 53/459 |
| 6,715,263 | B2 | * | 4/2004 | Banks | 53/425 |
| 7,361,317 | B2 | | 4/2008 | Bourne et al. | |
| 7,718,433 | B2 | | 5/2010 | Stecklein et al. | |
| 2006/0104856 | A1 | | 5/2006 | Farrell et al. | |
| 2007/0026472 | A1 | | 2/2007 | Prokash et al. | |

* cited by examiner

*Primary Examiner* — Thanh Truong
(74) *Attorney, Agent, or Firm* — Knox Patents; Thomas A. Kulaga

(57) ABSTRACT

Apparatus and a method for using a packaging system for a sterilizable item. The packaging system includes a first sleeve that is elongated and a second sleeve that encloses one end of the first sleeve. The first sleeve is an elongated open ended tube or pouch. The second sleeve is an open ended tube or pocket. The sides of the first sleeve and the sides of the second sleeve are proximate each other with the closed end of the first sleeve proximate a closed end of the second sleeve. The open end of the first sleeve is folded into a cuff that covers the open end of the second sleeve. In one embodiment, the apparatus includes a sterilization indicator affixed to the outside of the packaging system.

19 Claims, 3 Drawing Sheets

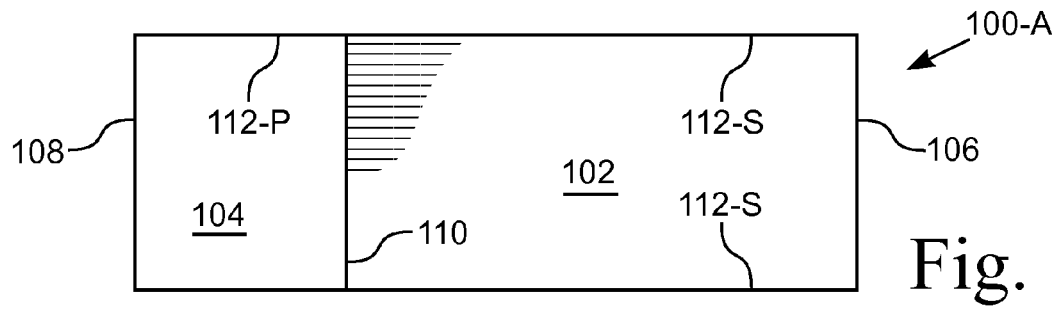
Fig. 1
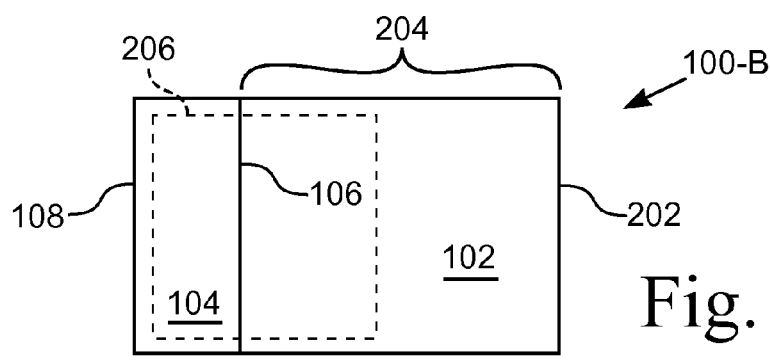
Fig. 2
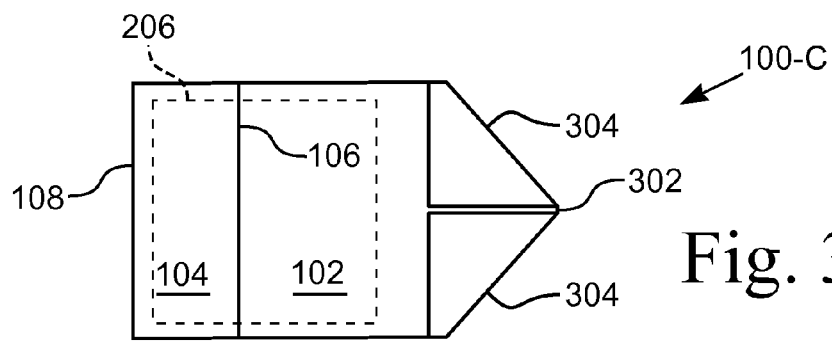
Fig. 3
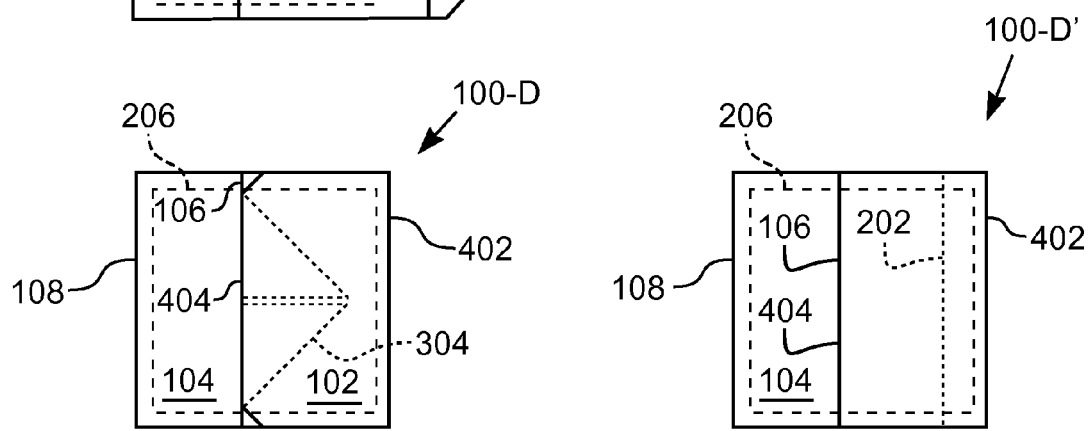
Fig. 4A
Fig. 4B

PACKAGING SYSTEM FOR A STERILIZABLE ITEM

CROSS-REFERENCE TO RELATED APPLICATIONS

This application claims the benefit of U.S. Provisional Application No. 61/303,435, filed Feb. 11, 2010.

STATEMENT REGARDING FEDERALLY SPONSORED RESEARCH OR DEVELOPMENT

Not Applicable

BACKGROUND

1. Field of Invention

This invention pertains to an improved packaging system and methods for using and manufacturing such a packaging system. The packaging system is for packaging a sterilizable item that allows aseptic introduction of a sterile item, particularly one that has been subjected to flash sterilization, into a sterile environment.

2. Description of the Related Art

During surgery, a sterile field is maintained for patient safety. All instruments and appliances entering the sterile field must be sterile. It is common practice to sterilize such instruments and appliances before the surgery and to introduce those instruments and appliances in a sterile manner. Various devices and methods are employed to maintain sterility during storage and introduction into the sterile field.

For example, U.S. Pat. No. 5,638,661, titled "Method and packaging system for packaging a sterilizable item," discloses one such system. The packaging system for the sterilizable item includes a sterilizable flexible elongate tubular member that forms a pouch. The item to be sterilized is placed in the tubular member, or pouch, near the closed end. The tubular member is folded closed and the packaging system and item are sterilized. After sterilization, the item can be dispensed from the sterile tubular member and transferred onto a sterile field by a single non-scrubbed attendant while maintaining the sterility and integrity of the item and the field. The construction of the tubular member is such that it is susceptible to flashover when handling, thereby compromising the sterility of the item.

It is also desirable to be able to determine if the item has been sterilized. Various devices and methods are employed to indicate sterility to operating room personnel. For example, U.S. Pat. No. 4,358,015, titled "Pressure sensitive closure pouch with insertable sterilization indicator," discloses a sterilizable pouch that has a strip of adhesive adjacent the mouth with a peelable release strip. The peelable release strip includes an indicator means for indicating its exposure to a predetermined sterilization condition. To use the pouch, an article is inserted within the pouch, the peelable release strip is removed from the adhesive and placed within the pouch next to the article, and the adhesive strip on one of the webs is brought into contact with the other web to close the mouth of the pouch. When the pouch is sterilized, the indicator means on the peelable release strip within the pouch changes appearance to indicate the attainment of the predetermined sterilization condition within the pouch. In such a system, the pouch must be opened and the peelable release strip removed from the pouch before determining if the article has been sterilized.

Another example is U.S. Pat. No. 7,718,433, titled "Packaging system for a sterilized article." The pouch includes an integral internal sterilization indicator. The sterilizing agent sensitive substance can be an indicator ink printed as an ink line on the interior of the sterilization pouch below the cuff. The indicator becomes visible during aseptic delivery of the packaged article to provide a clear indication as to whether or not adequate conditions for sterilization have been achieved.

BRIEF SUMMARY OF THE INVENTION

According to one embodiment of the present invention, a packaging system having a pouch with a pocket is provided. The pouch is a tubular sleeve. The tubular sleeve and the pocket are a non-woven material of a weight and porosity that prevents strike-through during and after flash sterilization. The tubular sleeve is elongated and, in one embodiment, formed from a single sheet. The closed end is formed by folding the sheet medial to opposing ends. The sides of the folded sheet are welded or otherwise sealed together to form a pouch with an open end opposite the closed end.

The pocket is formed from a single sheet that has a closed end formed by folding the single sheet medial to opposing ends. The sides of the folded sheet are welded or otherwise sealed to the side seams of the tubular sleeve such that the pocket is attached to the tubular sleeve. The tubular sleeve and the pocket together form a barrier proximate the closed end of the packaging system that is sufficient to prevent strike-through after flash sterilization. The non-woven material is sufficiently porous to allow the superheated steam to pass for sterilization, yet not so porous as to allow the sterilized item to be contaminated when a non-sterile person handles the outside of the packaging system at the closed end. The combined layers of the tubular sleeve and the pocket eliminate the need for a moisture barrier, which results in reduced sterilization time and easier disposal of the packaging system after use because the moisture barrier requires special processing not required by the non-woven material of the packaging system.

In one embodiment, an indictor tab is attached externally to the tubular sleeve. The indicator provides a visual indication that the packaging system has been exposed to conditions suitable to sterilize the contents of the packaging system. In one embodiment, the indicator has an adhesive backing that is positioned to seal the tubular sleeve to the pocket when in the folded configuration. In one such embodiment, the indicator is partially attached to a medial portion of the tubular sleeve such that when the tubular sleeve is folded, the unattached portion of the indicator is positioned to secure the tubular sleeve to the pocket with the tubular sleeve in the folded configuration. The unattached portion of the indicator has a backing adjacent the adhesive. When the tubular sleeve is folded into the folded configuration, the backing is removed and the indicator is adhered to the pocket.

A method of using the packaging system includes the step of inserting the item to be sterilized into the pouch and positioning the item proximate the pocket surrounding the closed end of the pouch. In one embodiment, a sterilization indicator is positioned proximate the item inside the pouch. After inserting the item, the portion of the pouch proximate the open end is folded over to form a cuff. The cuff is folded over and the end is tucked between the open end of the pouch and the pocket. In one embodiment, an adhesive backed indicator is affixed to the outside of the packaging system. In one such embodiment, the adhesive backed indicator is applied to connect the tubular sleeve to the pocket. After the packaging system is folded to contain the item, the packaging system and item are sterilized. After sterilization and before removing the item, the indicator is verified to indicate that the packaging system was sterilized. The end of the cuff is untucked and the cuff is pulled towards the closed end of the pouch, exposing the item for aseptic removal by a person in a sterile field.

BRIEF DESCRIPTION OF THE SEVERAL VIEWS OF THE DRAWINGS

The above-mentioned features of the invention will become more clearly understood from the following detailed description of the invention read together with the drawings in which:

FIG. 1 is a plan view of one embodiment of the packaging system;

FIG. 2 is a plan view of the packaging system with a folded cuff;

FIG. 3 is a plan view of the packaging system with a distal end of the cuff folded into a tucking-shape;

FIG. 4A is a plan view of the packaging system with the distal end of the cuff folded and tucked into the cuff;

FIG. 4B is a plan view of the packaging system showing an alternative tucked configuration;

DETAILED DESCRIPTION OF THE INVENTION

Figure 5:
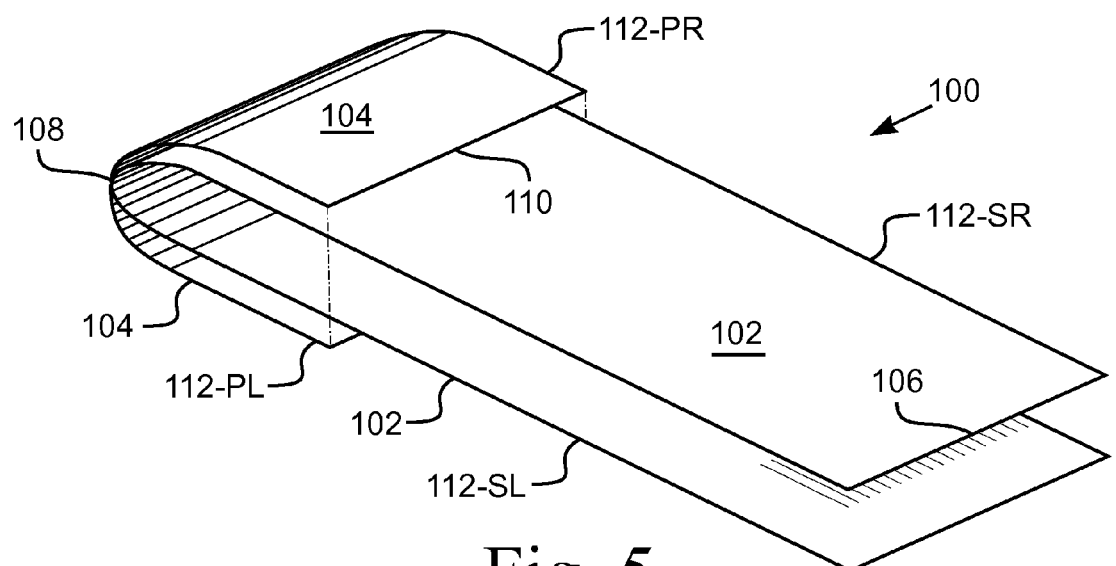
FIG. 5 is an exploded, perspective view of one embodiment of the packaging system.

Apparatus for a packaging system 100 for a sterilizable item 206 is disclosed. FIGS. 1 to 4 illustrate the packaging system 100 in progressive stages from an empty configuration (FIG. 1) to a packed or deployed configuration ready for sterilization and transport after sterilization (FIG. 4).

FIG. 1 illustrates a plan view of one embodiment of the packaging system 100. FIGS. 1 to 4 illustrate the packaging system 100 in various stages or configurations, 100-A, 100-B, 100-C, 100-D. The configuration of the packaging system 100-A illustrated in FIG. 1 is with the packaging system 100 laid out as it may be immediately after manufacturing or after being removed from a shipping or delivery package. Reference number 100 is used herein to refer to the packaging system 100 generally without referring to a specific configuration.

The illustrated packaging system 100-A includes a tubular sleeve 102 and a pocket 104. The tubular sleeve 102 is a pouch configured to receive objects 206. The tubular sleeve 102 is elongated with an open end 106 and a closed end 108. The edges 112 between the open end 106 and the closed end 108 are closed or sealed.

The pocket 104 has an open end 110 and a closed end 108 that is proximate to and covering the closed end 108 of the tubular sleeve 102. The edges 112-P of the pocket 104 are proximate the edges 112-S of the tubular sleeve 102. The distance between the closed end 108 and the open end 110 of the pocket 104 is no more than approximately one-third the distance from the closed end 108 and the open end 106 of the sleeve 102.

FIG. 2 illustrates a plan view of the packaging system 100-B with a folded cuff 204. The illustrated packaging system 100-B is folded between the open end 110 of the pocket 104 and the open end 106 of the tubular sleeve 102. The tubular sleeve 102 is folded such that the inside surface of the tubular sleeve 102 as illustrated in FIG. 1 is turned out to form a cuff 204. The cuff 204 has an open, or distal, end 202 that allows passage into the tubular sleeve 102. The open end 202 of the cuff 204 is located medially relative to the tubular sleeve 102. The cuff 204 has an opposite end 106 that is proximate the pocket 104. The opposite end 106 of the cuff 204 is the open end of the tubular sleeve 102.

The packaging system 100-B is dimensioned to receive an item 206 inside the tubular sleeve 102 and positioned proximate the closed end 108. The pocket 104 is dimensioned to accommodate the item 206 such that the item 206 is surrounded with at least two plies of material when the packaging system 100 is completed folded. The item 206 is one that is desired to be sterilized after it is placed in the tubular sleeve 102. Before sterilization, neither the item 206 nor the packaging system 100 are sterilized. After sterilization, the item 206 is handled aseptically by a person who is in a sterile field, and the packaging system 100 prevents the item 206 from being contaminated when handled by someone outside the sterile field. In the illustrated embodiment, the item 206 is shown as a rectangular object, but, persons skilled in the art would recognize that the item 206 can have any configuration and shape suitable for being contained in the packaging system 100.

FIG. 3 illustrates a plan view of the packaging system 100-C with an open end 202 of the cuff 204 folded into a tucking-shape. With the packaging system 100-C in a collapsed configuration that is substantially flat, the corners of the cuff 204 adjacent the cuffs open end 202 are folded over and form a pair of flaps 304. The pair of flaps 304 define a point 302 that is coincident with the open end 202 of the cuff 204 as illustrated in FIG. 2.

FIG. 4A illustrates a plan view of the packaging system 100-D with the distal end 202 of the cuff 204 folded and tucked into the opposite end 106 of the cuff 204. After folding the distal end 202 of the cuff 204 as illustrated in FIG. 2, the cuff 204 is folded medial to the distal end 202 and the open end 106 and the point 302 and a portion of the flaps 304 are tucked into the open end 106. The point 302 and the portion of the flaps 304 tucked into the open end 106 are retained by the open end 106 to form a self-sealed package 100-D.

The item 206 inside the packaging system 100-D as illustrated in FIG. 4 has a sterilizable/sterilized configuration. That is, the packaging system 100-D has a configuration that encloses the item 206 for placement into a sterilizer, such as a flash sterilizer. The same configuration is used to enclose the item 206 after sterilization to prevent contamination. The woven material of the tubular sleeve 102 and pocket 104 allows steam to contact all surfaces of the item 206 contained in the packaging system 100-D without being hindered by a moisture barrier, which inhibits steam transmission. Further, the pocket 104 and the closed end 108 of the tubular sleeve 102 prevents contamination during transfer of the item 106 to the sterile field.

After the item 206 is sterilized, the item 206 is kept in the packaging system 100-D and delivered to the sterile field by a person carrying the packaging system 100-D. The packaging system 100-D is easily opened for aseptic presentation of the sterilized item 206. A person who is not prepped for a sterile field grasps the closed end 108 of the packaging system 100-D. The tucked point 302 is removed from inside the open end 106 and the cuff 204 is allowed to assume the configuration 100-B illustrated in FIG. 2 where the cuff 204 does not have the flaps 304. The person uses their other hand to grasp the lip of the open end 106 and pull the cuff over the hand grasping the closed end 108. The person continues to pull the open end 106 over their wrist and arm to invert the tubular sleeve 102 and the pocket 104 to expose the sterilized item 206. After the sterilized item 206 is sufficiently exposed, the person is able to either place the item 206 inside the sterile field or hand off the item 206 to someone who is in the sterile field and able to aseptically handle the item.

FIG. 4B illustrates a plan view of the packaging system 100-D' showing a second tucked configuration. In the illustrated embodiment, the cuff 204 is folded with the distal end 202 tucked into the open end 106 on one side of the packaging system 100-D'. The distal end 202 is pushed inside the cuff 204 without any folds. The configuration of the packaging system 100-D' illustrated in FIG. 4B has less of a bulge from the unfolded distal end 202 of the cuff 204.

FIGS. 1 to 4B illustrate two embodiments of methods of using the packaging system 100. The first step is inserting the item 206 to be sterilized into the pouch, or tubular sleeve, 102 and positioning the item 206 proximate the pocket 104 surrounding the closed end 108 of the pouch 102. The pocket 104 is verified to be dimensioned such that the item 206 fits within the boundaries of the pocket 104. That is, the open end 110 of the pocket 104 extends past the item 206 that is proximate the closed end 108. In one embodiment, a step of positioning a sterilization indicator in the pouch is performed. Such a sterilization indicator provides confirmation that the item 206 itself was exposed to sterilization conditions. The portion of the pouch 102 proximate the open end 106 is folded over the tubular sleeve 102 to form a cuff 204 having an open end 202 and a distal end 106 that extends over a medial portion of the pocket 104. The step of folding the sleeve 102 to form a cuff 204 can be performed before or after the step of inserting the item 206 in the sleeve 102.

The open end 202 of the cuff 204 is folded and tucked between the pocket 104 and the open end 106 of the tubular sleeve 102. In one embodiment, the open end 202 of the cuff 204 is folded to form a point that is tucked into the open end 106 of the tubular sleeve 102 adjacent the pocket 104. In another embodiment, the cuff 204 is folded and the open end 202 of the cuff 204 is tucked directly between the pocket 104 and the open end 106 of the tubular sleeve 102.

In one embodiment, after the packaging system 100 is folded to contain the item 206, an indicator 702 is affixed to the outside of the pouch 102. In one such embodiment, the indicator 702 is adhesively attached to connect the tubular sleeve 102 to the pocket 104.

After the packaging system 100 is folded to contain the item 206, the packaging system 100 and the item 206 are sterilized. After sterilization and before removing the item 206, the indicator 702, if one is employed, is verified to indicate that the packaging system 100 has been sterilized by being exposed to the proper conditions. The item 206 is then presented aseptically to a person in a sterile field. The item 206 is presented aseptically by a person outside the sterile field grasping the pocket 104 and the item 206 inside. The open end 106 of the cuff 204 is untucked from between the open end 106 of the tubular sleeve 102 and the pocket 104. The open end 106 of the tubular sleeve 102 is pulled toward the closed end 108 of the pouch 102 until a portion of the item 206 is exposed sufficiently for a person in the sterile field to grasp the item 206 and remove it from the packaging system 100 after the other person releases the item 206 from his grasp. With the item 206 removed, the packaging system 100 can be disposed.

FIG. 5 illustrates an exploded, perspective view of the packaging system 100. The tubular sleeve 102 is a single sheet of material that is folded at the closed end 108. The pocket 104 is a single sheet of material that is folded at the closed end 108. To manufacture the packaging system 100, the sheets of material are brought together and the edges 112-PL, 112-SL on one side of the tubular sleeve 102 and pocket 104 are joined, such as by heat sealing. The edges 112-PR, 112-SRL on the other side of the tubular sleeve 102 and pocket 104 are also joined, such as by heat sealing. The joined edges 112-S form a tubular sleeve 102 with an open end 106 and a closed end 108. Likewise, the joined edges 112-P form a pocket 104 with an open end 110 and a closed end 108. In the illustrated embodiment the closed end of the tubular sleeve 102 is proximate the closed end 108 of the pocket 104.

The material of the tubular sleeve 102 and the pocket 104 is a thin, lightweight flexible fabric. The polyurethane material is suitable for heat sealing the edges 112 and is able to withstand the temperatures used by sterilizers. In one embodiment, the material is a non-woven material with about 30-40% porosity and a weight of 40 grams per square meter. In other embodiments, a heavier weight material is used. Also, in other embodiments, the color of the material is related to the material weight, thereby allowing a specific weight to be easily identified, such as would be used for a specific application.

Figure 6:
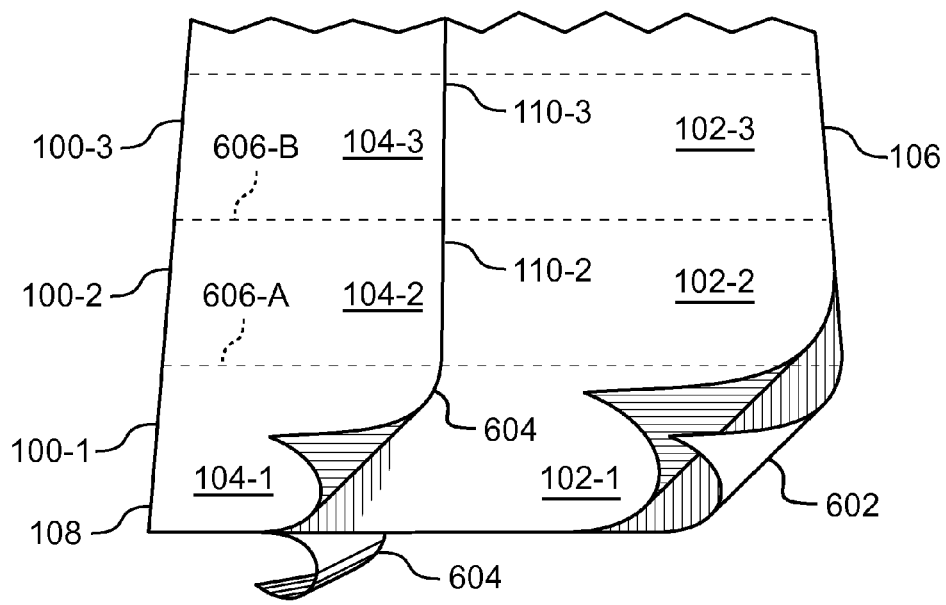
FIG. 6 is a perspective view of one embodiment of the two webs used to fabricate packaging systems.

FIG. 6 illustrates a perspective view of one embodiment of the two webs used to fabricate packaging systems 100-1, 100-2, 100-3. A first web 602 of material is folded in half lengthwise for a series of tubular sleeves 102-1, 102-2, 102-3. FIG. 6 shows adjacent corners of the first web 602 curled up to illustrated the folded material. A second web 604 of material is folded in half lengthwise for a series of pockets 104-1, 104-2, 104-3. FIG. 6 shows the corners of the second web 604 curled to illustrated the folded material being on opposite sides of the first web 602. The first web 602 is inside the second web 604 with the folded edges proximate each other. Parallel cut lines extend from the folded, closed end 108 to the open end 106 of the tubular sleeve 102. During fabrication, the webs 602, 604 are cut and the edges 112 are sealed to make individual packaging systems 100-1, 100-2, 100-3 from the web 602, 604.

Figure 7:
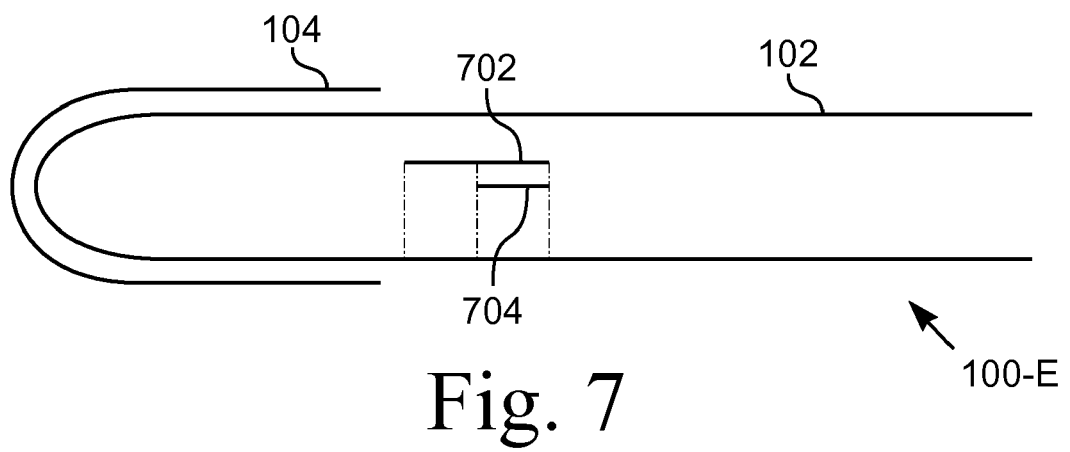
FIG. 7 is an exploded, side view of another embodiment of the packaging system showing an indicator.

FIG. 7 illustrates an exploded, side view of another embodiment of the packaging system 100-E showing an indicator 702. In the illustrated embodiment, an indictor 702 is positioned medially on the inside side of the tubular sleeve 102. The indicator 702 has an adhesive on the back surface with an adhesive protector 704 over a portion of the adhesive that is proximate the open end 106 of the tubular sleeve 102. The indicator 702 is positioned such that when the tubular sleeve 102 is folded, for example, as shown in FIG. 8, the adhesive protector 704 is removed and the unattached portion of the indicator 702 is adhered to the pocket 104.

Figure 8:
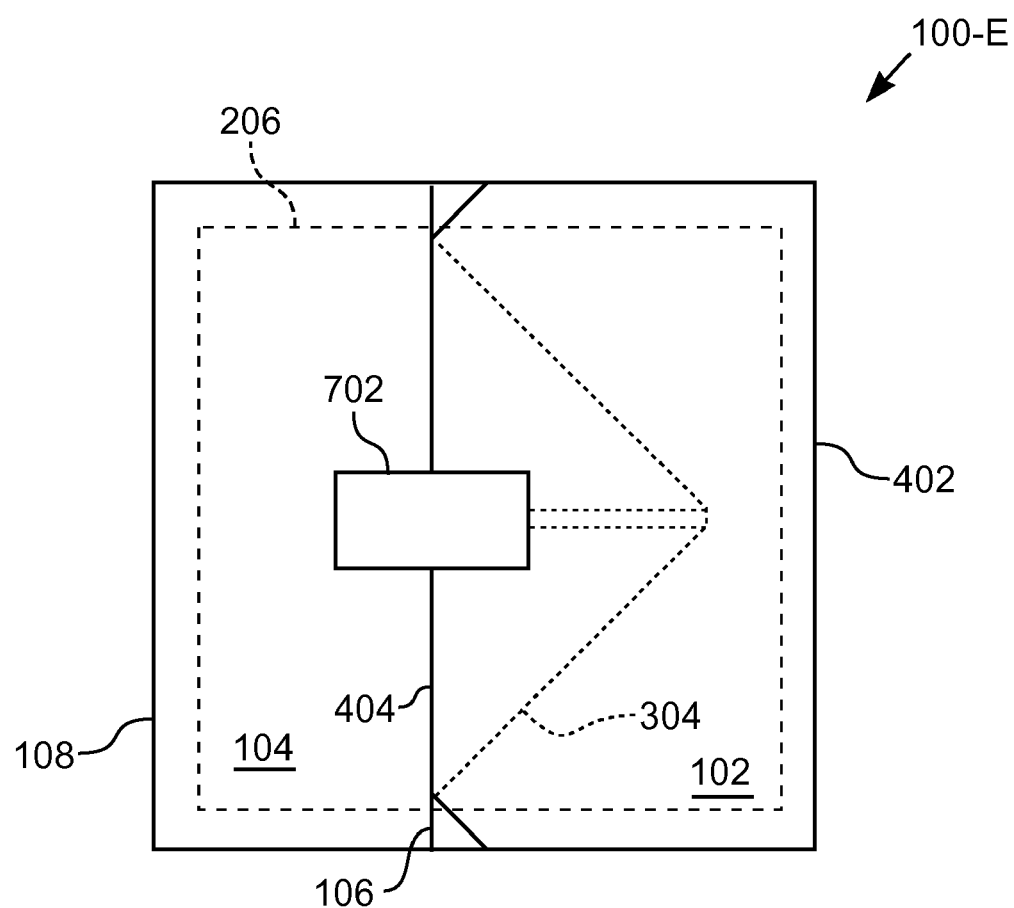
FIG. 8 is a plan view of another embodiment of the packaging system showing an indicator.

FIG. 8 illustrates a plan view of another embodiment of the packaging system 100-E showing an indicator 702. The indicator 702 provides a visual indication that the packaging system 100-E has been exposed to conditions suitable to sterilize the contents of the packaging system 100-E. In the illustrated embodiment, the packaging system 100-E has the distal end 202 of the cuff 204 folded and tucked into the opposite end 106 of the cuff 204 with an indicator 702 closing the packaging system 100-E. The indicator 702 is an adhesive backed flexible strip that has an outer surface that indicates if sterilization has occurred. Sterilization is indicated as occurring when the indicator 702 provides visual indication that the indicator 702 was exposed to conditions suitable to sterilize the contents of the packaging system 100-E.

In one embodiment, the indicator 702 has an adhesive protector 704 that covers a portion of the adhesive on the indicator 702. The indicator 702 is adhered to the tubular sheet 102 in such a position that when the packaging system 100-E is folded as illustrated, the portion of the indicator 702 with the adhesive protector 704 is positioned proximate the pocket 104. The adhesive protector 704 is removed and the indicator 702 is adhered to the pocket 104, thereby securing the packaging system 100-E in the folded configuration and providing indication of the sterilization status of the packaging system 100-E and the contained item 206.

The packaging system 100 includes various functions. The function of preventing strike-through is implemented, in one embodiment, by the adjacent layers of material of the pocket 104 and the tubular sleeve 102. The material has a porosity and weight sufficient to prevent migration of surface contaminates through the double layer of material. The juxtaposition of the pocket 104 relative to the adjacent tubular sleeve 102 creates an interface with an air gap that acts as an insulator that prevents contaminates from migrating from the outside surface of the pocket 104 to the item 206 inside the tubular sleeve 102.

The function of indicating if the item 206 has been sterilized is implemented, in one embodiment, by the indicator 702 affixed to the outside of the packaging system 100. In one embodiment, the indicator 702 has an adhesive backing and the indictor 702 is positioned across where the cuff 204 and the pocket 104 meet when the packaging system 100 is in a folded configuration. In one such embodiment, the indicator 702 is positioned medially along one side of the tubular sleeve 102 such that the indicator 702 is in position to be adhered to the pocket 104 when the packaging system 100 is in a folded configuration. In another embodiment, a second indicator is inserted in the tubular sleeve 102 proximate the item 206. The second indicator is only visible after the packaging system 100 is opened. The first indicator 702 provides indication that the packaging system 100 has been exposed to conditions suitable for sterilization. The second indicator provides indication that the item 206 itself has been exposed to conditions suitable for sterilization.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An apparatus for receiving a sterilizable item and allowing for aseptic introduction of the sterilizable item after sterilization, said apparatus comprising:
a first sleeve that is an elongated pouch, said first sleeve has an open end and a closed end opposite said open end, said first sleeve being permeable to steam; and
a second sleeve attached to said first sleeve, said second sleeve being permeable to steam, said second sleeve proximate said closed end of first sleeve, said second sleeve dimensioned to fully enclose the sterilizable item when the sterilizable item is proximate said closed end, said first sleeve having a length between said closed end and said open end sufficient for said first sleeve to form a cuff with said open end of said first sleeve between a closed end of said second sleeve and an open end of said second sleeve, said length sufficient for a distal end of said cuff to be tucked into and retained within a space defined by said open end of said first sleeve and said second sleeve when the item is inside said first sleeve, said space defined by an inside surface of said first sleeve with an entirety of said inside surface being permeable to steam from an outside surface of said second sleeve, wherein the item, when inside said first sleeve proximate said closed end of said first sleeve, is exposed to steam that penetrates said first and second sleeves; and wherein the apparatus is permeable to steam across an entire surface to which the sterilizable item is exposed.

2. The apparatus of claim 1 wherein said second sleeve extends no further than one third of the length of said first sleeve.

3. The apparatus of claim 1 wherein said first and second sleeves are a non-woven material.

4. The apparatus of claim 3 wherein said non-woven material has a porosity and a weight sufficient to prevent migration of contaminates through said first and second sleeves.

5. The apparatus of claim 3 wherein said non-woven material has a weight of approximately 40 grams per square meter.

6. The apparatus of claim 1 further including an indicator responsive to conditions suitable to sterilize the item, said indicator secured to an external surface of said first sleeve such that said indicator is visible when said first sleeve is folded with said distal end of said cuff tucked.

7. The apparatus of claim 6 wherein said indicator is further secured to an external surface of said second sleeve.

8. The apparatus of claim 6 further including a sterilization indicator inside said first sleeve, said sterilization indicator having indicia visible only after said apparatus is sterilized.

9. A method for packaging an item for aseptic introduction to a sterile field after sterilization, said method comprising:
(a) selecting a sleeve and a pocket that are permeable to steam wherein said sleeve is elongated and has a closed end opposite said open end, and said pocket surrounds said closed end of said sleeve wherein an entire portion of said closed end of said sleeve is permeable to steam applied to an outside surface of said pocket;
(b) inserting the item into an open end of said sleeve;
(c) positioning the item in said tubular sleeve proximate said pocket;
(d) folding said sleeve to form a cuff with said open end encircling a portion of said pocket, said cuff having a cuff end opposite said closed end of said sleeve; and
(e) after performing said steps (a), (b) and (c), tucking said cuff end into said open end such that said cuff end is secured between said pocket and a portion of said open end of said sleeve, whereby the item is secured in said sleeve and capable of being exposed to steam applied to the external surface of said sleeve and pocket, and wherein the apparatus is permeable to steam across an entire surface to which the item is exposed.

10. The method of claim 9 further including the steps of
(f) sterilizing the item inside said sleeve; and
(g) presenting the item aseptically to a person in a sterile field.

11. The method of claim 10 further including, before step (f) of sterilizing, a step of securing said cuff to said pocket with a sterilization indicator, said sterilization indicator having a surface with adhesive backing, and said sterilization indicator having indicia visible after said step (f) of sterilizing.

12. The method of claim 10 wherein said step (g) of presenting includes
(g1) grasping the item through said pocket;
(g2) releasing said cuff end from between said pocket and a portion of said open end of said sleeve; and (g3) pulling said cuff end toward and past said closed end of said sleeve until a portion of the item is exposed sufficiently for the person in said sterile field to grasp the item.

13. The method of claim 9 wherein said step (a) of selecting includes a step of selecting a material for said sleeve and said pocket, said material being non-woven with a porosity and a weight sufficient to prevent migration of contaminates through said material of said sleeve and said pocket.

14. The method of claim 9 wherein said step (a) of selecting includes a step of selecting a material for said sleeve and said pocket, said material being non-woven with a weight of approximately 40 grams per square meter.

15. The method of claim 9 wherein said step (e) of tucking includes the step of folding each corner of said cuff end that has been flattened and the step of tucking a distal end of said cuff end between said pocket and a portion of said open end of said sleeve.

16. The method of claim 9 further including, after said step (e) of tucking said cuff end, a step of verifying that the item is surrounded completely by at least two layers of material.

17. The method of claim 9 further including a step (f) of securing said cuff to said pocket with a sterilization indicator, said sterilization indicator having a surface with adhesive backing.

18. The method of claim 9 further including a step (f) of positioning an indicator, said indicator being responsive to conditions suitable to sterilize the item.

19. The method of claim 9 further including a step (f) of positioning an indicator such that said indicator is visible after performing step (e) of tucking, said indicator being responsive to conditions suitable to sterilize the item.

\* \* \* \* \*